(12) United States Patent
Lee et al.

(10) Patent No.: US 11,717,550 B2
(45) Date of Patent: Aug. 8, 2023

(54) METHOD FOR PREPARING DRINKING WATER FOR LIVESTOCK TO CREATE ENVIRONMENT FOR REVITALIZING INTESTINAL EFFECTIVE MICROORGANISMS USING TREATMENT OF COMPONENTS VIA ION EXCHANGE OF NATURAL MINERALS

(71) Applicants: Sang-Kuk Lee, Uijeongbu-si (KR); Yong-Suk Lee, Uijeongbu-si (KR)

(72) Inventors: Sang-Kuk Lee, Uijeongbu-si (KR); Yong-Suk Lee, Uijeongbu-si (KR)

(73) Assignees: Sang-Kuk Lee; Yong-Suk Lee

( * ) Notice: Subject to any disclaimer, the term of this patent is extended or adjusted under 35 U.S.C. 154(b) by 0 days.

(21) Appl. No.: 17/546,272

(22) Filed: Dec. 9, 2021

(65) Prior Publication Data

US 2022/0096585 A1  Mar. 31, 2022

Related U.S. Application Data

(63) Continuation of application No. PCT/KR2021/010851, filed on Aug. 17, 2021.

(30) Foreign Application Priority Data

Sep. 2, 2020 (KR) .......................... 10-2020-0111424

(51) Int. Cl.
*A61K 36/42* (2006.01)
*A61P 1/14* (2006.01)
(Continued)

(52) U.S. Cl.
CPC ................ *A61K 36/42* (2013.01); *A23L 2/00* (2013.01); *A61K 9/0095* (2013.01); *A61K 9/08* (2013.01);
(Continued)

(58) Field of Classification Search
CPC ........ A61K 36/42; A61K 9/0095; A61K 9/08; A61K 33/04; A61K 33/26; A61K 33/32;
(Continued)

(56) References Cited

FOREIGN PATENT DOCUMENTS

KR  1020020024127 A  3/2002
KR  1020030000937 A  1/2003
(Continued)

OTHER PUBLICATIONS

Korean Notice of Allowance (KR 10-2020-0111424), KIPO, dated Dec. 28, 2020.

*Primary Examiner* — Brent T O'Hern
(74) *Attorney, Agent, or Firm* — Park & Associates IP Law Office

(57) ABSTRACT

A method for preparing drinking water for livestock includes mixing 2.5 to 5.0 WT % of tourmaline and 2.5 to 5.0 WT % of illite as natural minerals in powder form of 2 to 3 μm with 90 to 95 WT % of water to produce a mixed solution, and maintaining the mixed solution for 5 to 7 hours at room temperature, and removing the tourmaline powders and illite powders to produce leachate; mixing 15 to 25 WT % of detoxified sulfur in powder form of 2 to 3 μm, 10 to 25 WT % of Rrhus verniciflua Stokes extract, and 10 to 25 WT % of Momordicae Semen extract with 25 to 65 WT % of the leachate to produce a liquid mixture, and maintaining the liquid mixture for 12 hours; and mixing 150 to 250 ml of the liquid mixture with 20 l of water and maintaining the liquid mixture for 6 to 7 hours for amplification.

1 Claim, 6 Drawing Sheets

(51) Int. Cl.
*A61K 9/00* (2006.01)
*A61K 9/08* (2006.01)
*A61K 33/04* (2006.01)
*A61K 33/26* (2006.01)
*A61K 33/32* (2006.01)
*A61K 36/22* (2006.01)
*A23L 2/00* (2006.01)
*A23L 2/38* (2021.01)
*A23L 33/00* (2016.01)

(52) U.S. Cl.
CPC .............. *A61K 33/04* (2013.01); *A61K 33/26* (2013.01); *A61K 33/32* (2013.01); *A61K 36/22* (2013.01); *A61P 1/14* (2018.01); *A23L 2/38* (2013.01); *A23L 33/00* (2016.08)

(58) Field of Classification Search
CPC ... A61K 36/22; A61P 1/14; A23L 2/00; A23L 33/00; A23L 2/38
USPC .......................................................... 426/590
See application file for complete search history.

(56) References Cited

FOREIGN PATENT DOCUMENTS

| KR | 1020090120528 A | | 11/2009 |
|---|---|---|---|
| KR | 1020110018538 A | | 2/2011 |
| KR | 2020110007331 U | | 7/2011 |
| KR | 20120058116 A | * | 6/2012 |
| KR | 1020120058116 A | | 6/2012 |
| KR | 1020130076656 A | | 7/2013 |
| KR | 1020160099207 A | | 8/2016 |
| KR | 1020170059124 A | | 5/2017 |

* cited by examiner

```
┌─────────────────────────────────────────────────┐
│ Mixing 2.5 to 5.0WT% of tourmaline and 2.5 to   │
│ 5.0WT% of illite as natural minerals in a       │
│ powder particle form of 2 to 3 μm with 90 to    │──S101
│ 95WT% of water to produce a mixed solution,     │
│ and maintaining the mixed solution for 5 to 7   │
│ hours at room temperature, and removing the     │
│ tourmaline powders and the illite powders to    │
│ produce leachate                                │
└─────────────────────────────────────────────────┘
                         │
                         ▼
┌─────────────────────────────────────────────────┐
│ Mixing 15 to 25WT% of detoxified sulfur in a    │
│ powder particle form of 2 to 3μm, 10 to 25WT%   │
│ of Rrhus verniciflua Stokes (RVS) extract, and  │──S102
│ 10 to 25WT% of Momordicae Semen extract with    │
│ 25 to 65WT% of the leachate produced in the     │
│ S101 to produce a liquid mixture, and           │
│ maintaining the liquid mixture for 12 hours     │
└─────────────────────────────────────────────────┘
                         │
                         ▼
┌─────────────────────────────────────────────────┐
│ Mixing 150 to 250 ml of the liquid mixture      │
│ produced in the S102 with 20L of water and      │──S103
│ maintaining the mixture for 6 to 7 hours for    │
│ amplification                                   │
└─────────────────────────────────────────────────┘
```

FIG. 1

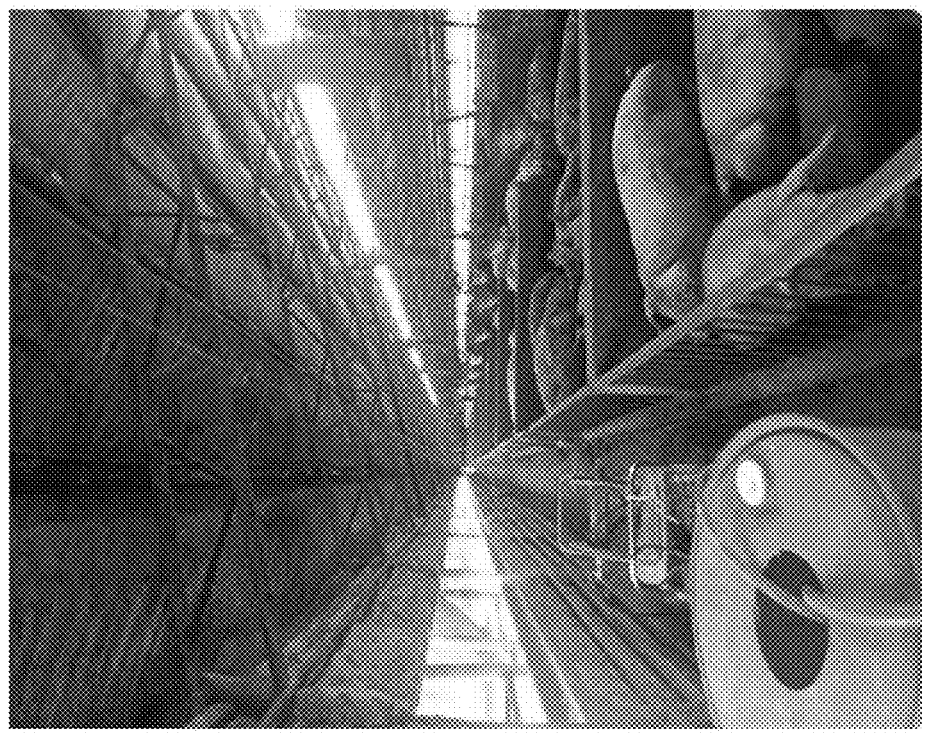
<State after drinking water for livestock is administered to pigs>
<State before drinking water for livestock is administered to pigs>
FIG. 5

METHOD FOR PREPARING DRINKING WATER FOR LIVESTOCK TO CREATE ENVIRONMENT FOR REVITALIZING INTESTINAL EFFECTIVE MICROORGANISMS USING TREATMENT OF COMPONENTS VIA ION EXCHANGE OF NATURAL MINERALS

REFERENCE TO RELATED APPLICATIONS

This is a continuation of International Patent Application PCT/KR2021/010851 filed on Aug. 17, 2021, which designates the United States and claims priority of Korean Patent Application No. 10-2020-0111424 filed on Sep. 2, 2020, the entire contents of which are incorporated herein by reference.

FIELD OF THE INVENTION

The present disclosure relates to a method for preparing drinking water for livestock. More specifically, the present disclosure relates to a method for preparing drinking water for livestock in which detoxified sulfur, and beneficial ingredients of Rrhus verniciflua Stokes (RVS), and Momordicae Semen may be treated to be more easily absorbed into a body of the livestock via ions exchange action of natural minerals including tourmaline and illite, thereby creating an environment stimulating and for revitalizing intestinal effective microorganisms of the livestock.

BACKGROUND OF THE INVENTION

Water is the source of all life, is essential for the metabolism of all living things, including humans, and is used as an important resource for agricultural activities, industrial activities, and other human activities and thus has an absolute value.

Such water is one of the important nutrients in livestock. An amount of drinking water which the livestock takes is twice an amount of a feed intake. The water plays a number of important roles in the body, including transporting the feed to the digestive system, transporting nutrients that are components of blood to each organ, helping the absorption of nutrients, excreting wastes and toxins out of the body, and maintaining the body temperature.

Thus, many livestock farms take groundwater near a livestock house and supply the same as drinking water for the livestock. Instead of supplying the groundwater containing various impurities and bacteria in a non-filtered manner, water treatment is performed to meet the water quality requirements for disease prevention.

However, the livestock drinking water does not contain sufficient ingredients necessary for growth. Thus, Korean Patent No. 1546254 discloses a method for treating drinking water for livestock using deep sea water. However, most of livestock farms are located in inland areas far from the shore in which deep sea water is taken. Thus, a transportation cost to transport a large amount of deep sea water to livestock farms is high. Storage for storing the deep sea water is required in the livestock farms. When the deep sea water is stored for a long time, there is a problem that there is a risk of contamination by harmful microorganisms.

Therefore, in order to promote the growth of livestock and increase resistance to various diseases, vitamins and beneficial microorganisms may be added to the drinking water. However, under the reality that livestock is raised in a confined space, antibiotics are widely used for the prevention and treatment of diseases and as a growth promoter.

However, as the use of the antibiotics is regulated worldwide due to residual oil in livestock and resistance problems, the antibiotics are used only to treat diseases of livestock. Thus, the need for alternative substances to the antibiotics that may promote growth while significantly lowering the disease incidence of the livestock has increased.

In other words, the misuse of antibiotics in livestock has caused many controversies, such as a decrease in resistance to specific diseases, a decrease in anti-viral ability, and a residual problem in the livestock products. Thus, research on alternative substances that do not have concerns about antibiotic resistance or residues is being actively conducted.

The alternative substances to the antibiotic including probiotics, organic acids, prebiotics, enzymes, plant extracts, etc. are attracting attention. The alternative substances exhibit various mechanisms and actions in the digestion and metabolism of livestock.

The plant extracts use plants that have been used as spices or medicines in the East and the West since ancient times, and contain various physiologically active substances and nutrients.

In addition, medicinal plants have been used only for oriental medicine treatment and preparation of functional health food. However, recently, their advantages and safety are being studied as alternative substances due to regulations on the use of antibiotics in livestock. Various physiologically active ingredients for antibacterial, antioxidant, antiviral functions, anti-toxin, maintenance of microbial flora of effective promoting enzyme activity, and immune activity may be taken by the livestock to boost metabolism, strengthen immunity, and increase appetite, and improve digestion, and the like.

Accordingly, a concentration of active ingredients exhibiting physiological activity when being supplied to livestock varies depending on the type of the medicinal plant. In order to maximize the effect thereof, various combinations thereof and appropriate concentration control are required. However, there are limitations such as cumbersomeness.

Further, as consumers' lifestyles change toward the pursuit of well-being that values health and the environment, awareness of the safety of livestock products due to the mass use of chemical ingredients and antibiotics is spreading, and thus the consumption of eco-friendly livestock products is increasing.

Prior art literature: Patent Literature: Patent No. 1546254 (Title of the disclosure: A method for treating drinking water for livestock using deep sea water).

SUMMARY OF THE INVENTION

A purpose of the present disclosure is to provide a method for preparing drinking water for livestock in which detoxified sulfur, and beneficial ingredients of Rrhus verniciflua Stokes (RVS), and Momordicae Semen may be treated to be more easily absorbed into a body of the livestock via ions exchange action of natural minerals including tourmaline and illite, thereby creating an environment stimulating and for revitalizing intestinal effective microorganisms of the livestock.

One aspect of the present disclosure provides a method for preparing drinking water for livestock to create an environment for revitalizing intestinal effective microorganisms using treatment of components via ion exchange of natural minerals, the method comprising: S101: mixing 2.5 to 5.0 WT % of tourmaline and 2.5 to 5.0 WT % of illite as natural minerals in a powder particle form of 2 to 3 μm with 90 to 95 WT % of water to produce a mixed solution, and maintaining the mixed solution for 5 to 7 hours at room temperature, and removing the tourmaline powders and the illite powders to produce leachate; S102: mixing 15 to 25 WT % of detoxified sulfur in a powder particle form of 2 to 3 μm, 10 to 25 WT % of Rrhus verniciflua Stokes (RVS) extract, and 10 to 25 WT % of Momordicae Semen extract with 25 to 65 WT % of the leachate produced in the S101 to produce a liquid mixture, and maintaining the liquid mixture for 12 hours; and S103: mixing 150 to 250 ml of the liquid mixture produced in the S102 with 20 L of water and maintaining the mixture for 6 to 7 hours for amplification.

According to the method for preparing drinking water for livestock to create an environment for revitalizing intestinal effective microorganisms using treatment of components via ion exchange of natural minerals, an action of the detoxified sulfur to perform the body's antioxidation and protect cells and detoxify the internal organs that interfere with digestion, and an action of reducing blood clots and relieving inflammation via the urushiol and facetin components of Rrhus verniciflua Stokes (RVS), and an action of Momordicae Semen to alleviate stomach inflammation may be enhanced because the detoxified sulfur, and the beneficial ingredients of RVS and Momordicae Semen may be treated to be absorbed more easily into the body of the livestock via exchange between the ions of tourmaline and illite as leached in the water, thereby creating an environment for revitalizing intestinal effective microorganisms, and continuously maintaining the environment to increase digestion and immunity. Thus, the growth of livestock is promoted, and the disease incidence of livestock may be significantly reduced with minimal use of harmful antibiotics or without the use of antibiotics. In particular, the method has the effect of providing eco-friendly livestock products that do not cause the harmful problem of accumulating antibiotics to people who eat meat containing herbal ingredients that does not contain any antibiotics or chemicals.

Thus, even when the livestock are grown in a limited space, the detoxified sulfur, and beneficial ingredients of RVS, and Momordicae Semen may be treated to be absorbed more easily into the digestive system of the livestock via exchange between the ions of tourmaline and illite such that and digestive enzymes may be increased through revitalization of intestinal effective microorganisms, thereby maintaining the optimal temperature in the body to improve immune diseases and increase feed absorption efficiency. Further, the drinking water may reduce mortality of the livestock and increase the growth thereof, thereby to produce high-quality organic meat products having the improved taste and meat quality.

BRIEF DESCRIPTION OF THE DRAWINGS

FIG. 1 is a diagram showing a method for preparing drinking water for livestock to create an environment for revitalizing intestinal effective microorganisms using treatment of components via ion exchange of natural minerals according to an embodiment of the present disclosure.

FIG. 5 is a diagram showing quality of a pig meat in a pig farm A taking drinking water for livestock produced by the method according to an embodiment of the present disclosure.

DETAILED DESCRIPTION OF THE INVENTION

Figure 2:
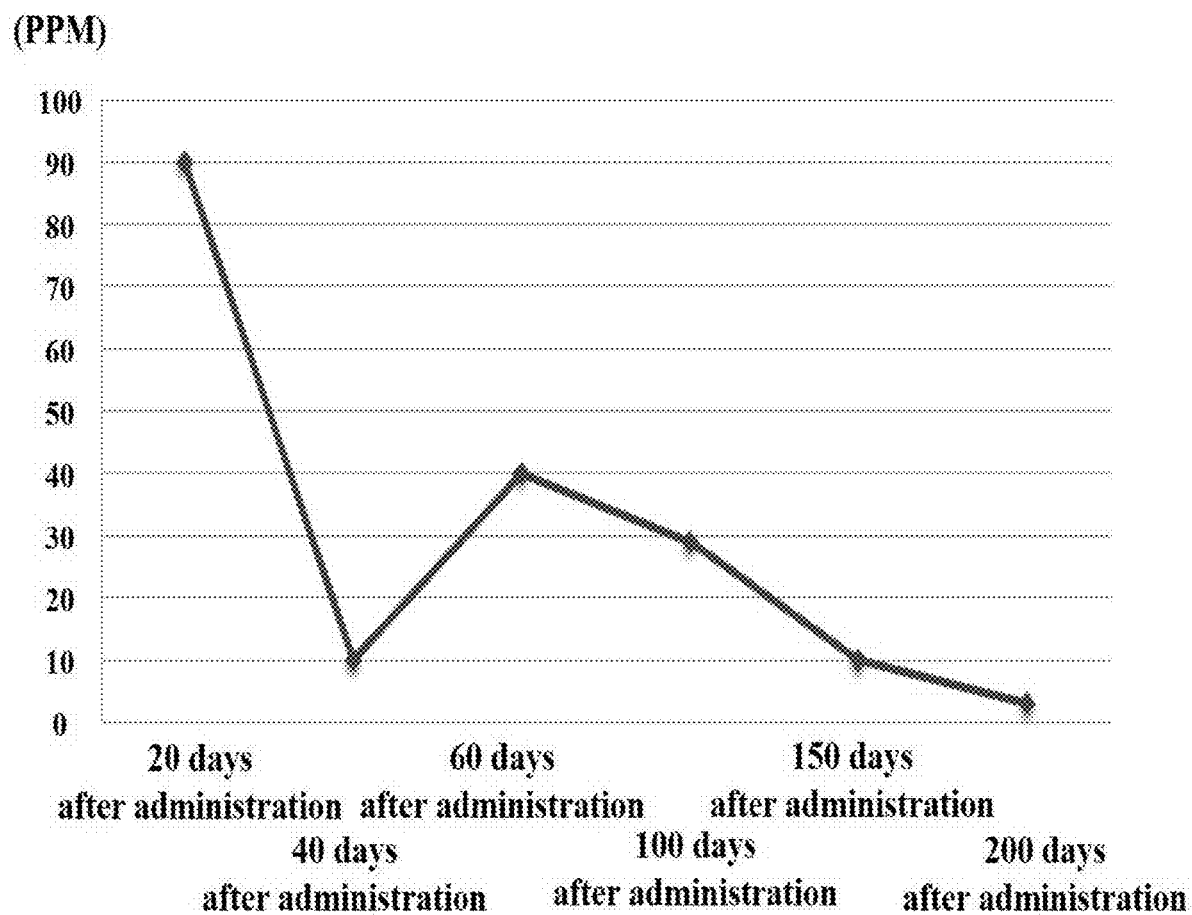
FIG. 2 is a diagram showing change in an ammonia concentration over time after administering drinking water for livestock produced by the method according to an embodiment of the present disclosure to pigs of a pig farm A.

Hereinafter, a preferred embodiment of the present disclosure will be described in detail with reference to the accompanying drawings. The embodiment is intended to be described in detail so that a person of ordinary skill in the art to which the disclosure belongs can easily implement the disclosure. The technical spirit and scope of the present disclosure is limited thereto.

FIG. 1 is a diagram showing a method for preparing drinking water for livestock to create an environment for revitalizing intestinal effective microorganisms using treatment of components via ion exchange of natural minerals according to an embodiment of the present disclosure.

The drinking water for livestock prepared by the method according to an embodiment of the present disclosure may contain detoxified sulfur, Rrhus verniciflua Stokes (RVS), and Momordicae Semen. Further, ions of the natural minerals including tourmaline and illite may freely move and exchange with each other in the drinking water, thereby allowing the detoxified sulfur, and beneficial ingredients of Rrhus verniciflua Stokes (RVS) and Momordicae Semen to be absorbed more easily into the body, thereby creating an environment for revitalization of intestinal effective microorganisms of the livestock.

Specifically, as shown in FIG. 1, the method for preparing drinking water for livestock according to an embodiment of the present disclosure may include S101: mixing 2.5 to 5.0 WT % of tourmaline and 2.5 to 5.0 WT % of illite as natural minerals in a powder particle form of 2 to 3 μm with 90 to 95 WT % of water to produce a mixed solution, and maintaining the mixed solution for 5 to 7 hours at room temperature, and removing the tourmaline powders and the illite powders to produce leachate; S102: mixing 15 to 25 WT % of detoxified sulfur in a powder particle form of 2 to 3 μm, 10 to 25 WT % of Rrhus verniciflua Stokes (RVS) extract, and 10 to 25 WT % of Momordicae Semen extract with 25 to 65 WT % of the leachate produced in the S101 to produce a liquid mixture, and maintaining the liquid mixture for 12 hours; and S103: mixing 150 to 250 ml of the liquid mixture produced in the S102 with 20 L of water and maintaining the mixture for 6 to 7 hours for amplification. Then, the drinking water for livestock prepared by the method according to an embodiment of the present disclosure may flow for 4 to 5 hours in the supply pipe and thus be fed to the livestock. In this connection, the detoxified sulfur, and beneficial ingredients of Rrhus verniciflua Stokes (RVS), and Momordicae Semen which improve the growth of livestock and contribute to the production of high-quality organic meat products may be absorbed more easily into the body via the ion exchange action of the natural mineral components including tourmaline and illite in water. Thus, an environment for stimulation and revitalization of the intestinal effective microorganism of livestock may be created and continuously maintained, thereby enhancing digestion and immunity of the livestock.

99% of a body mass may be composed of oxygen, carbon, hydrogen, nitrogen, calcium and phosphorus, and the remaining 1% thereof may be composed of potassium, sulfur, sodium, chlorine and magnesium. Although sulfur appears to be relatively insignificant in the composition thereof, in fact, sulfur is the third most abundant mineral in the body. One of the important functions of sulfur is an antioxidation.

The detoxified sulfur as a constituent component according to an embodiment of the present disclosure is present in all living tissues, is contained in two important amino acids, one of which is methionine, which is mainly obtained from egg whites and fish. The methionine is an essential amino acid that cannot be synthesized in the body and is obtained from the outside. The other thereof is cysteine, which requires a certain percentage of sulfur and is synthesized in the body.

The detoxified sulfur acts as the antioxidant and protects cells, detoxifies the internal organs that interfere with digestion, forms essential amino acids, and protects beneficial bacteria, specifically reduces infections with fungi and parasites, and maintain skin and hair, and claws healthy, maintains collagen synthesis and cartilage flexibility, reduces inflammation, relieves allergies and acts as an antioxidant, improves cell membrane permeability to allow nutrients to be easily absorbed, and removes wastes, detoxifies through blood circulation, and heals wounds, and boosts immunity of livestock.

In an embodiment of the present disclosure, the detoxified sulfur is used in the powder form of 2 to 3 μm.

Rrhus verniciflua Stokes (RVS) as a component according to an embodiment of the present disclosure is known as a mysterious drug with both toxicity and pharmaceutical ability, and has been used for food and medicine for a long time in the East, and reduces blood clots and relieves inflammation and inhibits cell transformation via urushiol and pacetin thereof. In Donguibogam, dried Rrhus verniciflua Stokes (RVS) reduces blood clots, makes the intestines function well, kills parasites, and relieves fatigue. In Sinnongbonchogyeong, RVS is effective for fractures, numbness, and neuralgia. Further, it is recorded in Myeonguibyeolrok that RVS is effective in eliminating cough, back pain caused by digestive disorders, and eliminating roundworms by improving the function of the small intestine.

This Rrhus verniciflua Stokes (RVS) acts as an excellent preservative and insecticide that kills parasites in the human body and eliminates inflammation by blocking various bacteria. RVS preserves the cells of the human body so that they do not get damaged, while the Rrhus verniciflua Stokes (RVS) poison is known to have excellent anticancer effects by eliminating poisons caused by various cancers and diseases and preventing them from resurrecting.

Further, the sap of Rrhus verniciflua Stokes (RVS) contains urushiol. Based on a result of experimenting with urushiol at 3 to 4 PPM concentration, it was identified that urushiol has excellent anticancer activity to kill cancer cells. In particular, it was analyzed that the sap of Rrhus verniciflua Stokes (RVS) from Wonju, Gangwon province contains nearly 50% of urushiol.

Further, MU2 which has excellent anticancer effect was extracted upon analyzing urushiol from Rrhus verniciflua Stokes (RVS) sap. MU2 extracted from a product obtained by heat treatment of Rrhus verniciflua Stokes (RVS) tree has an excellent anticancer effect, and it more effective in inhibiting the growth of animal blood cancer cells, human lung cancer cells and gastric cancer cells than tetraplatin as the existing anticancer drug is.

In an embodiment of the present disclosure, Rrhus verniciflua Stokes (RVS) is used in the form of the extract obtained by cutting the Rrhus verniciflua Stokes (RVS) tree into small pieces and heating the bark or the pieces in water and filtering the solids through a mesh.

Momordicae Semen as a component according to an embodiment of the present disclosure is a seed of Momordica cochichinensis Springer belonging to a perennial Cucurbitaceae plant widely distributed in southern China and Vietnam. Momordicae Semen has the appearance of the turtle. The skin thereof may be removed and the remaining core may be extracted into a liquid form. The extract has a warm and sweet taste, protects the gastric mucosa, treats and relieves gastritis, removes toxins from various boils, and relieves breast lumps and treats back pain symptoms.

Momordicae Semen are used in the extract liquid. The extract liquid may be produced by peeling the skin and extracting the remaining core under reflux using water or alcohol or a liquid mixture thereof according to a widely used method for extracting conventional herbal medicines.

Further, tourmaline as the natural mineral according to an embodiment of the present disclosure has the property that the crystal itself thereof constantly generates electricity. Even when crushing the crystal into a very small size, (+) and (−) polarities are present at both ends of the crystal, respectively. The tourmaline may be composed mainly of Mg which is effective for cell revitalization, cardiac strengthening, nervous system, B which promotes growth and development, and is effective for skin and mucous membranes, Si which strengthens the inner portion of the skin and has a good effect on the kidneys, liver, and intestines, and Ca which acts to promote bone growth. In tourmaline, various anions may be generated via irregular shaking of natural atoms in a complex structure to promote intestinal digestion of livestock, thereby enhancing growth and immunity.

In an embodiment of the present disclosure, the tourmaline generates ions. In a state in which tourmaline ions freely move together with illite in the water, the generated ions are continuously delivered to illite to promote, strengthen, and maintain ionization of illite, thereby exchanging ions with each other. The tourmaline content based on 100 WT % of a total weight of the mixture of water and tourmaline and illite may be in a range of 2.5 to 5.0 WT %.

In addition, illite as the natural mineral according to an embodiment of the present disclosure is a common mineral in sedimentary rocks or hydrothermal metamorphic rocks. Illite has a clay-like structure in its mineralogical structure. The chemical composition thereof may include $SiO_2$, $Al_2O_3$, $K_2O$. Illite is formed at a relatively high temperature compared to other clay minerals. Because K+ exists between layers thereof, its use is expanding from an environmental point of view. Illite may emit negative ions and far-infrared rays in a natural state to adsorb particulate matters or separate particulate matters of different sizes from each other, and thus may have excellent adsorption, deodorization and decomposition power of heavy metals and toxic gases, high far-infrared radiation at room temperature, ability to generate negative ions, antibacterial and antiviral abilities, etc. In addition, illite strengthens non-specific immunity in the animal body, exhibits a healing effect on specific diseases, improves metabolism, such as promoting growth, and increases immunity by helping blood circulation through cell activation.

In an embodiment of the present disclosure, while illite freely moves in the form of natural mineral ions together with tourmaline in the water, illite is strongly ionized in a balanced manner with tourmaline ions. As in tourmaline, the illite content based on 100 WT % of a total weight of the mixture of water and tourmaline and illite may be in a range of 2.5 to 5.0 WT %.

The method may include mixing 2.5 to 5.0 WT % of tourmaline and 2.5 to 5.0 WT % of illite as natural minerals in a powder particle form of 2 to 3 μm with 90 to 95 WT % of water to produce a mixed solution, and maintaining the mixed solution for 5 to 7 hours at room temperature, and removing the tourmaline powders and the illite powders to produce leachate in S101.

In the leachate produced in the S101, the ions generated from the tourmaline in water promote and strengthen the mineral ionization of illite. The ion exchange between ions of tourmaline and illite is continuously performed so that the illite maintains the enhanced ionized state. For this purpose, the mixed solution may be maintained for 5 to 7 hours at room temperature to produce the leachate.

In this connection, the content of each of tourmaline and illite based on 100 WT % of a total weight of the mixture of water and tourmaline and illite may be in a range of 2.5 to 5.0 WT %. When the content of each of tourmaline and illite based on 100 WT % of a total weight of the mixture of water and tourmaline and illite is below a range of 2.5 to 5.0 WT %, the effectiveness of the natural minerals decreases. When the content of each of tourmaline and illite based on 100 WT % of a total weight of the mixture of water and tourmaline and illite is above the range of 2.5 to 5.0 WT %, a proportion of one natural mineral increases, while that of the other mineral decreases, there may be a problem that the effectiveness of the other natural mineral decreases.

The method may include mixing 15 to 25 WT % of detoxified sulfur in a powder particle form of 2 to 3 μm, 10 to 25 WT % of Rrhus verniciflua Stokes (RVS) extract, and 10 to 25 WT % of Momordicae Semen extract with 25 to 65 WT % of the leachate produced in the S101 to produce a liquid mixture, and maintaining the liquid mixture for 12 hours in S102.

In this connection, the content of the detoxified sulfur in a powder particle form of 2 to 3 μm may be in a range of 15 to 25 WT % based on a 100 WT % of a total weight of the mixture of the leachate, the detoxified sulfur, RVS extract, and Momordicae Semen extract. The content of each of Rrhus verniciflua Stokes (RVS) extract, and Momordicae Semen extract may be in a range of 10 to 25 WT % based on a 100 WT % of a total weight of the mixture of the leachate, the detoxified sulfur, RVS extract, and Momordicae Semen extract. When each content is lower than each predetermined range, there may be a problem in that the effect of the corresponding component is reduced. When each content exceeds each predetermined range, there may be a problem that the effect of the corresponding components is reduced while the contents of the other components are increased.

In addition, the mixture of 15 to 25 WT % of detoxified sulfur in a powder particle form of 2 to 3 μm, 10 to 25 WT % of Rrhus verniciflua Stokes (RVS) extract, and 10 to 25 WT % of Momordicae Semen extract with 25 to 65 WT % of the leachate produced in the S101 may be maintained for 12 hours at room temperature, thereby allowing the components to be fully activated.

Then, the method may include mixing 150 to 250 ml of the liquid mixture produced in the S102 with 20 L of water and maintaining the mixture for 6 to 7 hours for amplification in S103.

The drinking water for the livestock as produced through the above process may be supplied to the livestock while flowing for 4 to 5 hours through a water faucet. Thus, an action of the detoxified sulfur to perform the body's anti-oxidation and protect cells and detoxify the internal organs that interfere with digestion, and an action of reducing blood clots and relieving inflammation via the urushiol and facetin components of Rrhus verniciflua Stokes (RVS), and an action of Momordicae Semen to alleviate stomach inflammation may be enhanced because the detoxified sulfur, and the beneficial ingredients of RVS and Momordicae Semen may be treated to be absorbed more easily into the body of the livestock via exchange between the ions of tourmaline and illite as leached in the water, thereby creating an environment for revitalizing intestinal effective microorganisms, and continuously maintaining the environment to increase digestion and immunity. Thus, the growth of livestock is promoted, and the disease incidence of livestock may be significantly reduced with minimal use of harmful antibiotics or without the use of antibiotics. In particular, the method has the effect of providing eco-friendly livestock products that do not cause the harmful problem of accumulating antibiotics to people who eat meat containing herbal ingredients that does not contain any antibiotics or chemicals. Thus, even when the livestock are grown in a limited space, the detoxified sulfur, and beneficial ingredients of RVS, and Momordicae Semen may be treated to be absorbed more easily into the digestive system of the livestock via exchange between the ions of tourmaline and illite such that and digestive enzymes may be increased through revitalization of intestinal effective microorganisms, thereby maintaining the optimal temperature in the body to improve immune diseases and increase feed absorption efficiency. Further, the drinking water may reduce mortality of the livestock and increase the growth thereof, thereby to produce high-quality organic meat products having the improved taste and meat quality.

EXAMPLE

First, 3.5 g of tourmaline which generates ions, and 3.5 g of illite which maintains balance of the ionized state while exchanging ions with tourmaline as natural minerals in the powder form of 2 to 3 μm were mixed with 100 g of water and the mixture was maintained at room temperature for 6 hours, and then the tourmaline and illite powders were removed to produce the leachate.

Next, 30 g of detoxified sulfur in the powder form, 25 g of Rrhus verniciflua Stokes (RVS) extract, and 25 g of Momordicae Semen extract were mixed with 100 g of the leachate. The liquid mixture was maintained for 12 hours at room temperature.

Then, 150 ml of the liquid mixture was mixed with 20 L of water in consideration of ease of work or the effect, and then the mixture was maintained for 6 to 7 hours to prepare the drinking water for livestock.

The drinking water for the livestock as produced according to an embodiment of the present disclosure was administered to pigs on the pig farm A while flowing the same for 4 to 5 hours via a water faucet in the pig farm A which had a complaint about a serious odor problem.

FIG. 2 is a diagram showing change in an ammonia concentration over time after administering drinking water for livestock produced by the method according to an embodiment of the present disclosure to pigs of the pig farm A.

As shown in FIG. 2, the odor was reduced by 90% after 40 days of administration. After 3 months, the odor in the external parking lot of the Pig Farm A substantially disappeared. Further, the number of the flies was significantly reduced, and the residents around the pig farm A confirmed that the odor had disappeared in the rainy day.

Figure 3:
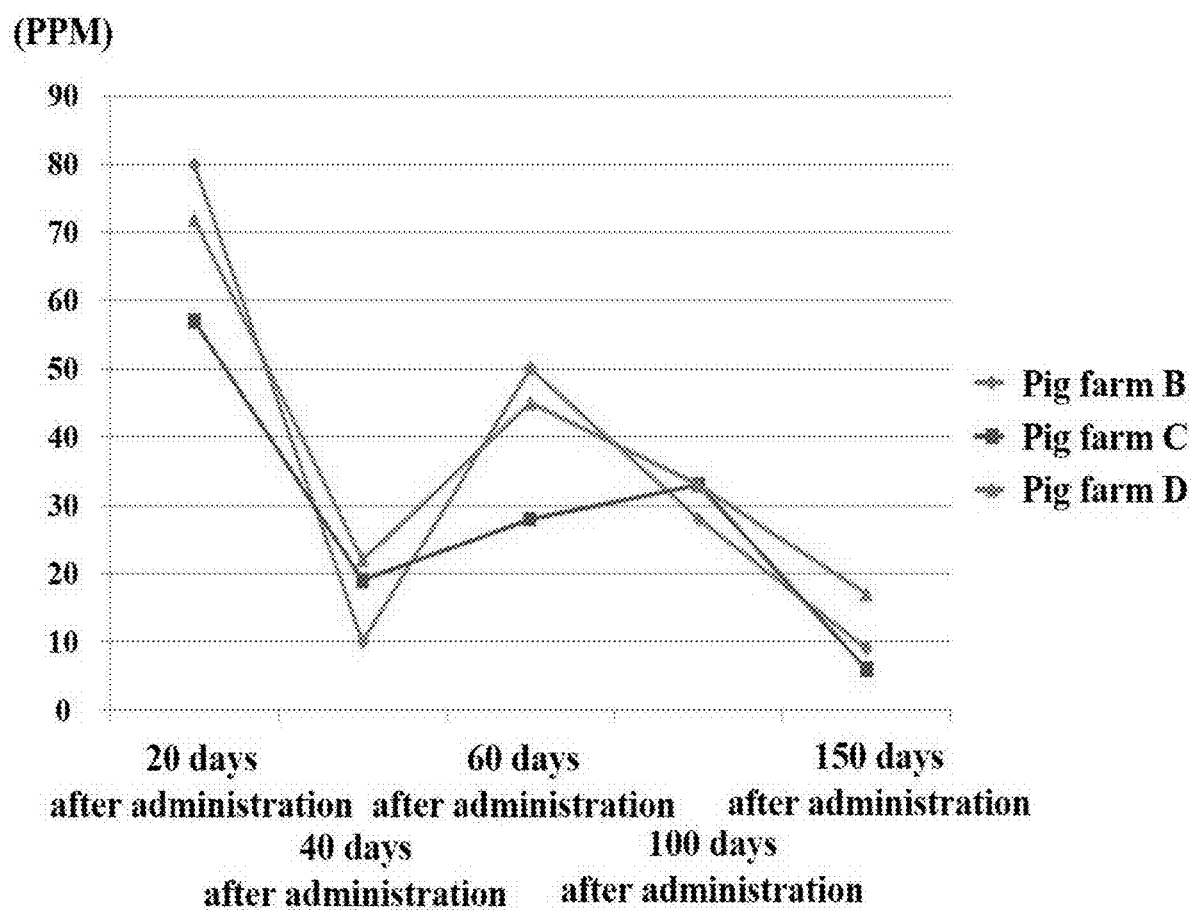
FIG. 3 is a view showing a state of a compost and manure treatment place in which a bad odor is converted to a fermentation smell after drinking water for livestock produced by the method according to an embodiment of the present disclosure is administered to pigs of a pig farm A.

FIG. 3 is a view showing a state of a compost and manure treatment place in which a bad odor is converted to a fermentation smell after drinking water for livestock produced by the method according to an embodiment of the present disclosure is administered to pigs of a pig farm A.

As shown in FIG. 3, after the administration to pigs, the bad odor in the compost place was changed to the smell of fermentation, and the manure treatment place was changed to a good state.

Figure 4:
FIG. 4 is a diagram showing a state of a pig farm A before and after administration of drinking water for livestock produced by the method according to an embodiment of the present disclosure to pigs therein.

FIG. 4 is a diagram showing a state of a pig farm A before and after administration of drinking water for livestock produced by the method according to an embodiment of the present disclosure to pigs therein.

As shown in FIG. 4, it may be identified that there is a large difference before and after administration of the drinking water for the livestock prepared by the method according to an embodiment of the present disclosure to the pigs. The administration of the drinking water may decrease the ammonia concentration significantly from 90 PPM to 5 PPM. Accordingly, the inside of the farm was changed from a dirty state to a clean state.

FIG. 5 is a diagram showing quality of a pig meat in a pig farm A taking drinking water for livestock produced by the method according to an embodiment of the present disclosure.

As shown in FIG. 5, it may be confirmed that the pigs taking the livestock drinking water has denser cells and vivid meat color, and has no fishy smell, had firm meat quality, and abundant flesh.

Figure 6:
FIG. 6 is a diagram showing change in an ammonia concentration over time after administration of drinking water for livestock prepared by the method according to an embodiment of the present disclosure to pigs in pig farms B, C, and D.

FIG. 6 is a diagram showing change in an ammonia concentration over time after administration of drinking water for livestock prepared by the method according to an embodiment of the present disclosure to pigs in pig farms B, C, and D.

As shown in FIG. 6, it may be identified that the odor was significantly reduced after administration. In the pig farm B, the gas generation in the barn was significantly reduced since 2 months after the administration, and the administration of drugs for the prevention and treatment of diseases, etc. was reduced by 50%.

Further, in the pig farm C, the stress of workers due to severe gas generation was significantly reduced, unlike before the administration. In the pig farm D, it was confirmed that the odor of the compost was converted to the smell of fermentation and the flies disappeared since 1 month after the administration.

In accordance with the present disclosure, the ion exchange action of the natural mineral minerals such as tourmaline and illite may allow the detoxified sulfur which acts as the body's antioxidants and protects cells and the detoxification action of internal organs that interferes with digestion, and urushiol and pacetin of Rrhus verniciflua Stokes (RVS) which reduce blood clots and perform inflammatory relieving action to be more easily absorbed to the body of the livestock. Thus, the intestinal microbes are revitalized, and internal temperature of the body of the livestock rises due to inhalation of drinking water and increase in digestive enzymes, thereby improving immune diseases without the use of minimal or no antibiotics. This may increase the feed efficiency, thereby obtaining eco-friendly livestock products while solving the chronic problem of the livestock grown in a limited space.

The present disclosure is not limited to the above embodiments, and various modifications are possible within the scope of the disclosure described in the claims, and such modifications are also included within the scope of the present disclosure.

What is claimed is:

1. A method for preparing drinking water for livestock to create an environment for revitalizing intestinal effective microorganisms using treatment of components via ion exchange of natural minerals, the method comprising:
    mixing 2.5 to 5.0 WT % of tourmaline powders and 2.5 to 5.0 WT % of illite as natural minerals in a powder particle form of 2 to 3 µm with 90 to 95 WT % of water to produce a mixed solution, and maintaining the mixed solution for 5 to 7 hours at room temperature, and removing the tourmaline powders and illite powders to produce leachate;
    mixing 15 to 25 WT % of detoxified sulfur in a powder particle form of 2 to 3 µm, 10 to 25 WT % of Rrhus verniciflua Stokes (RVS) extract, and 10 to 25 WT % of Momordicae Semen extract with 25 to 65 WT % of the leachate to produce a liquid mixture, and maintaining the liquid mixture for 12 hours; and
    mixing 150 to 250 ml of the liquid mixture with 20 l of water and maintaining the liquid mixture for 6 to 7 hours for amplification.

\* \* \* \* \*